United States Patent
Graff et al.

(10) Patent No.: US 6,843,131 B2
(45) Date of Patent: Jan. 18, 2005

(54) METHOD OF DETECTING DISCONTINUITIES ON ELONGATED WORKPIECES

(75) Inventors: Alfred Graff, Essen (DE); Friedhelm Schlawne, Duisburg (DE)

(73) Assignee: Mannesmannröhren, Mülheim Werke AG (DE)

( * ) Notice: Subject to any disclaimer, the term of this patent is extended or adjusted under 35 U.S.C. 154(b) by 0 days.

(21) Appl. No.: 10/425,997

(22) Filed: Apr. 29, 2003

(65) Prior Publication Data

US 2003/0233879 A1 Dec. 25, 2003

(30) Foreign Application Priority Data

Apr. 29, 2002 (DE) .......................................... 102 20 946

(51) Int. Cl.⁷ .............................................. G01N 29/10
(52) U.S. Cl. ........................................ 73/602; 73/622
(58) Field of Search ........................ 73/602, 620, 621, 73/622, 623

(56) References Cited

U.S. PATENT DOCUMENTS 3,916,699 A * 11/1975 Moran et al. ................. 73/623
4,307,612 A * 12/1981 Elsley et al. .................. 73/613
5,681,995 A * 10/1997 Ooura et al. .................. 73/622

FOREIGN PATENT DOCUMENTS

| DE | 36 22 500 A1 | 1/1988 | |
|----|---|---|---|
| DE | 39 43 226 C2 | 7/1990 | |
| JP | 05322860 A | * 12/1993 | .......... G01N/29/10 |

* cited by examiner

Primary Examiner—Hezron Williams
Assistant Examiner—Rose M. Miller
(74) Attorney, Agent, or Firm—Henry M. Feiereisen

(57) ABSTRACT

In a method of detecting discontinuities on elongated workpieces, in particular tubes and bars, using ultrasonic testing system, a test object is positioned in relationship to a test head of the testing system, with the test object and the test head being moveable to one another. Signals from the test head are transmitted to an evaluation unit, where they are digitized and evaluated. The digitized signals of a test shot of a length position X are compared with digitized signals of a test shot of a length position X+ΔX, wherein ΔX is a multiple of a shot distance, and the difference is evaluated.

6 Claims, 5 Drawing Sheets

METHOD OF DETECTING DISCONTINUITIES ON ELONGATED WORKPIECES

CROSS-REFERENCES TO RELATED APPLICATIONS

This application claims the priority of German Patent Application, Serial No. 102 20 946.4, filed Apr. 29, 2002, pursuant to 35 U.S.C. 119(a)-(d), the disclosure of which is incorporated herein by reference.

BACKGROUND OF THE INVENTION

The present invention relates to a method of detecting discontinuities on elongated workpieces, in particular on tubes and bars, using ultrasound.

German patent publication DE 36 22 500 A1 discloses a process and apparatus for the detection of discontinuities on cylindrical tubes and bars. Discontinuities are detected by moving the test object past stationary transmission and receiving transducers, which detect tangentially circulating guided wave pulses in the test object, whereby the amplitudes of the sequentially received signals are processed in a computer by forming a quotient to determine defects. The received signals are synchronized for evaluation with burst signals of the same frequency, a suitable time period and start delay, and transmitted to a peak detector. The amplitudes are digitized and transmitted to a computer.

German patent publication DE 39 43 226 C2 discloses a process for the detection of discontinuities on elongated workpieces, in particular on tubes and bars, using ultrasonic inspection. In the disclosed process, the test object is moved without rotation in an axial direction past a stationary electrodynamic transducer. Clocked wave pulses which circulate tangentially in the test object and propagate in two circumferential directions are received at a receiving site which is shifted relative to the transmission site by one quarter of the wavelength of the confined waves. The location of reception and the excitation of the wave pulses propagating simultaneously in both circumferential directions of the test object is selected such that both uninterfered circulating waves destructively interfere at the site of the receiver. For each cycle, the reception signal and a burst signal which has a high pulse duty ratio and period selected to be less than one quarter of the revolution time of the wave pulses about the test object and a length that corresponds to the decay time of the unobstructed wave pulses, is transmitted to a peak detector. The output signal of the peak detector is digitized and transmitted to a computer.

Both these conventional process suffer shortcomings because very short discontinuities, e.g. a hole, or discontinuities in unfavorable location may not be detected due to a low signal level.

It would therefore be desirable and advantageous to provide an improved process of detecting discontinuities on elongated workpieces to obviate prior art shortcomings and to enable a detection of short defects in the workpiece.

SUMMARY OF THE INVENTION

According to one aspect of the present invention, a method of detecting discontinuities on elongated workpieces, in particular tubes and bars, using ultrasonic testing system, includes the steps of positioning a test object in relationship to a test head of the testing system, with the test object and the test head being moveable to one another, generating reception signals with the test head and digitizing the signals for transmission to an evaluation unit, comparing the digitized signals of a test shot of a length position X with digitized signals of a test shot of a length position X+ΔX, wherein ΔX is a multiple of a shot distance; and evaluating a difference.

The present invention resolves prior art problems by using a differential technique which allows a safe detection even of short defects. The method according to the present invention has an advantage compared, for example, to a conventional differential technique used in testing eddy currents and described in a brochure by the company Förster "Wirbelstromprüfung mit Defektomat {Eddy-Current Test with Defektomat], page 2, by eliminating a complicated construction with two transducers offset at a length distance, including required electronics.

According to another feature of the present invention, the distance ΔX is freely selectable and not fixed by the selected distance between both transducers.

Depending on the existing computing power, it may be suitable to limit the number of signals subject to evaluation. The number of evaluated signals may be limited per test shot to a range between 20 and 100, e.g. 60 signals. Of course, higher numbers, e.g. 2000 signals, are also possible.

In general, the differential process according to the present invention is applicable for any type of generated reception signals. The advantage of the differential process according to the present invention is especially favorable when the structure of the reception signals is complicated. An example involves reflection indications by Lamb waves generated in the test object. This type of inspection, may be expanded by generating alternatively in the test clock cycle two wave pulses at two sites located in circumferential direction, with the wave pulses propagating in both circumferential directions. In this case, the differential process can be applied to both the reflected pulses and the attenuated pulses.

Another application can involve the inspection of longitudinal seams. This inspection typically runs the testing unit along the weld seam and operates it in a clock cycle of a test shot. In this testing method, the received signal of a path coordinate X can also be associated with a receiving signal of a path coordinate X+ΔX, and subsequently differentiated.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
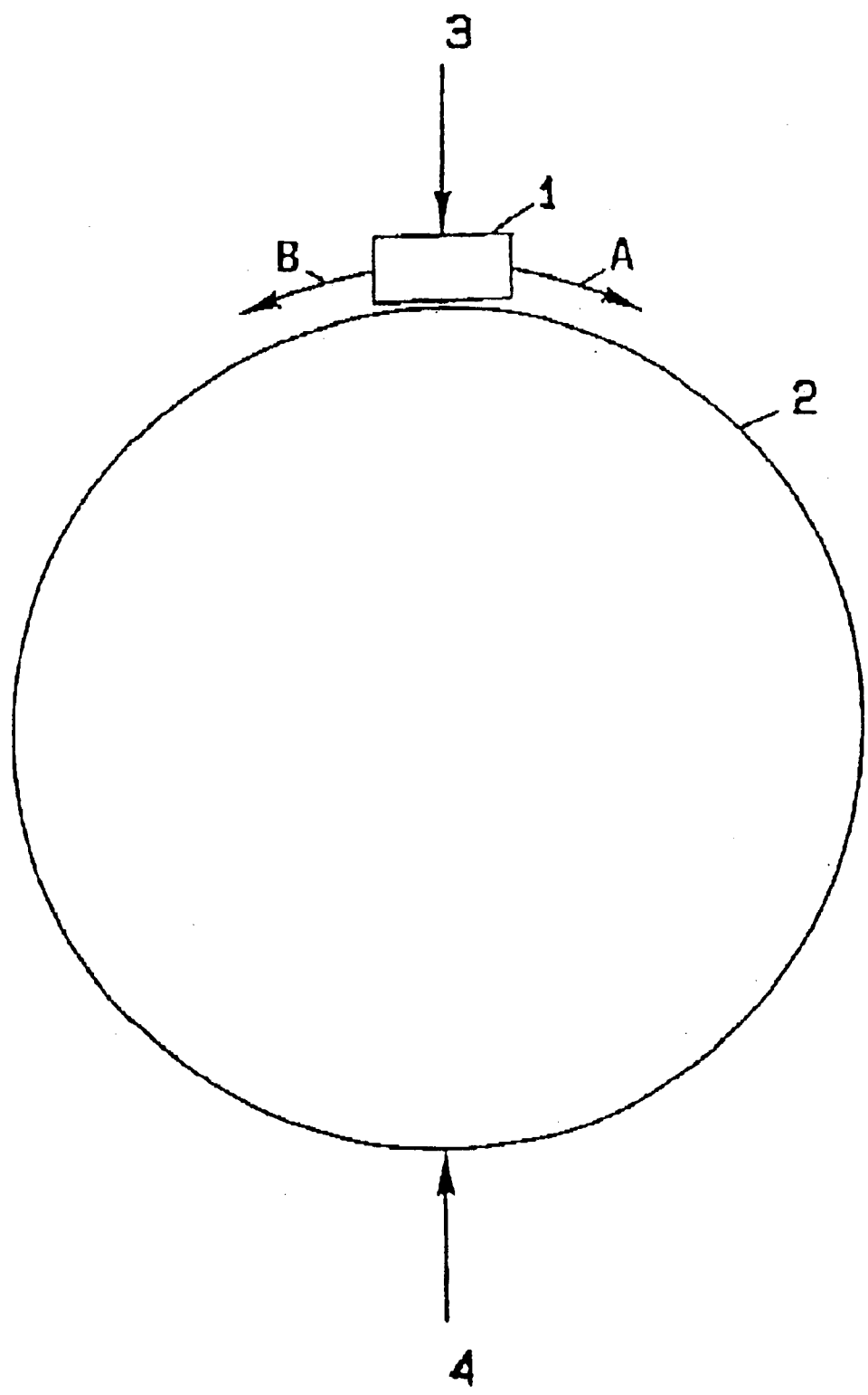
FIG. 1 is a basic diagram of a first exemplified embodiment for carrying out an evaluation process according to the present invention.

Throughout all the Figures, same or corresponding elements are generally indicated by same reference numerals.

These depicted embodiments are to be understood as illustrative of the invention and not as limiting in any way.

Turning now to the drawing, and in particular to FIG. 1, there is shown a basic diagram of a first exemplified embodiment for carrying out an evaluation process according to the present invention. A transducer 1 located at a certain distance from a test object 2 simultaneously emits a wave pulse A, B in both circumferential directions. In FIG. 1, the wave pulse emitted in the clockwise direction is designated by index A, and the wave pulse emitted in the counterclockwise direction is designated by index B. Both wave pulses A, B circulate several times in the circumferential direction and meet at two defined points of the circumference: once at the transducer 1 itself, here designated position 3, and on the side exactly opposite by 180°, here designated position 4. In the exemplary embodiment of FIG. 1, the receiving transducer is positioned precisely at the location where both uninterfered circulating wave pulses A, B interfere destructively.

For carrying out the testing process, two configurations are possible, one in which the transducer 1 is only a transmitting transducer, and the receiving transducer (not shown in FIG. 1) is located in position 4. This configuration is typically only rarely used since the precise positioning and calibration of the receiving transducer is very difficult. Alternatively, the transmitting and receiving coils can be interleaved in the transducer 1 and wound so as to be offset from one another by one quarter of the wavelength of the guided waves.

Figure 2:
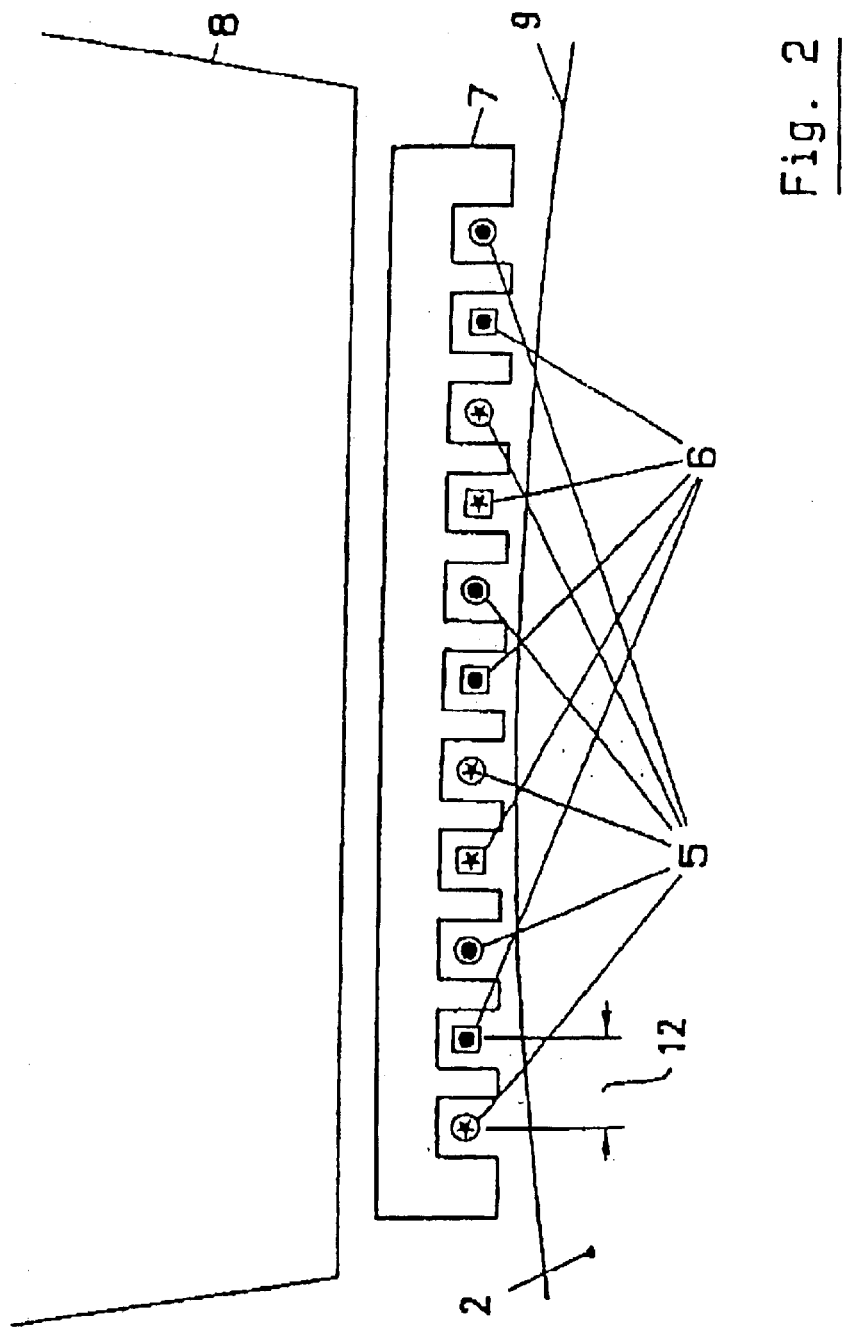
FIG. 2 is a schematic illustration of a transducer of the evaluation technique shown in FIG. 1.

FIG. 2 shows the details of the transducer 1. It can be seen that a bobbin 7 is arranged between a surface 9 of the test object 2 and a magnet 8 or magnet system. The transmitting and receiving windings 5, 6 are interleaved on the bobbin 7 and wound such that a distance 12 between two adjacent windings is one quarter of the wavelength.

Figure 3:
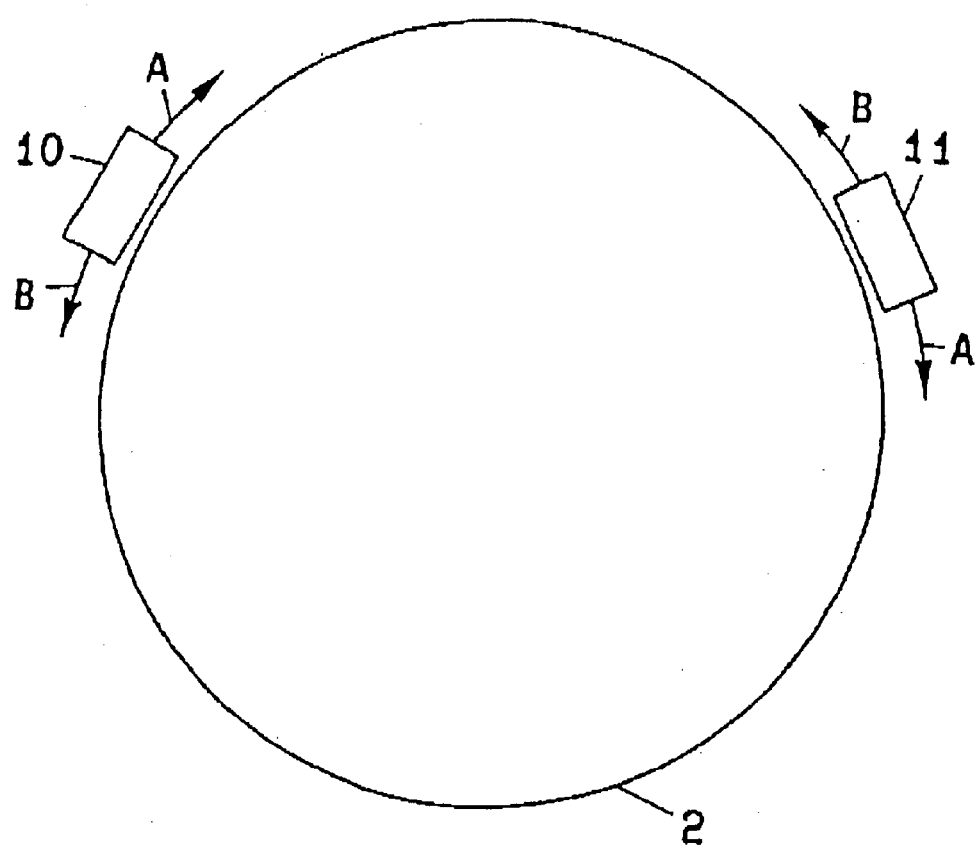
FIG. 3 is a basic diagram of a second exemplified embodiment for carrying out an evaluation process according to the present invention.

Turning now to FIG. 3, there is shown a basic diagram of a second exemplified embodiment for carrying out an evaluation process according to the present invention, utilizing the pulse-reflection technique and the transmission technique at the same time. Hereby, two separate electrodynamic transducers 10, 11 are disposed on the circumference of the test object 2. Suitably, the transducers 10, 11 are positioned at an offset of 90° and have transmitting and receiving windings 5 and 6 offset by one quarter of the wavelength (see FIG. 2). The transmitter coils of both transducers are operated in alternating fashion. In the first clock cycle, the transmitting coil of the transducer 10, located on the left in FIG. 3, transmits, and the receiving coil of the transducer 11, located on the right, measures the amplitudes of the circulating waves and transmits the sequentially received signals to an evaluation unit (not shown). At the same time, the receiving coil of the transducer 10 on the left side measures signals, i.e. reflection signals or signals generated by the non-uniform attenuation of the waves circulating in both directions. These signals are also transmitted to the evaluation unit. The signals measured in the receiving coil of the transducer 11 on the right side, e.g. the sum of the amplitudes of the first two peaks, can additionally be used for roughly monitoring the coupling of the receiving coil of the left transducer 11 since this receiving coil is integrated in the transmitting coil of the transducer 10. For the second clock cycle, excitation and/or reception in the two transducers 10, 11 is interchanged.

Figure 4A:
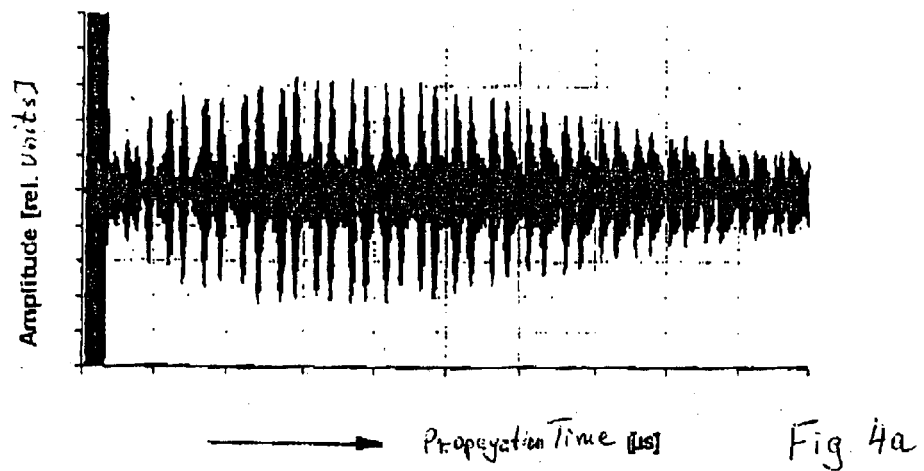
FIG. 4a shows the amplitude as a function of propagation time for reflection.
Figure 4B:
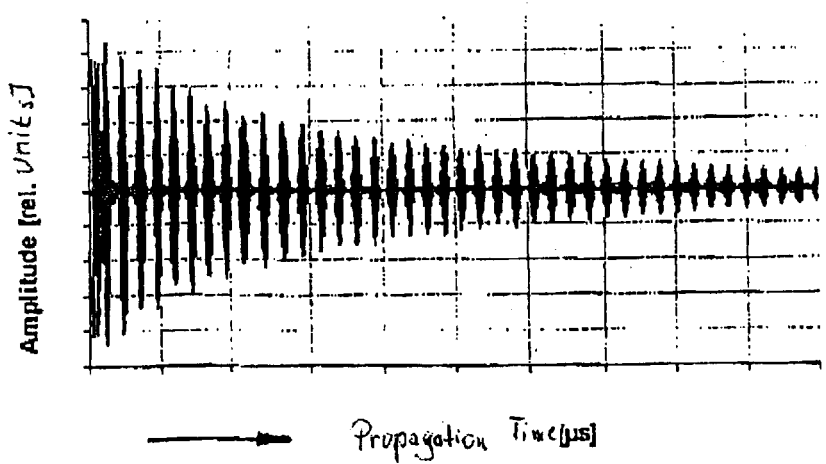
FIG. 4b shows the amplitude as a function of propagation time for attenuation.

FIGS. 4a and 4b show exemplified graphical illustrations of complicated signal sequences caused by a defect in the test object 2. FIG. 4a shows a sequence of reflection signals, wherein the amplitude is plotted as a function of the propagation time in $\mu$s. FIG. 4b shows a sequence of attenuation signals, wherein the amplitude is also plotted as a function of the propagation time in $\mu$s.

Figure 5:
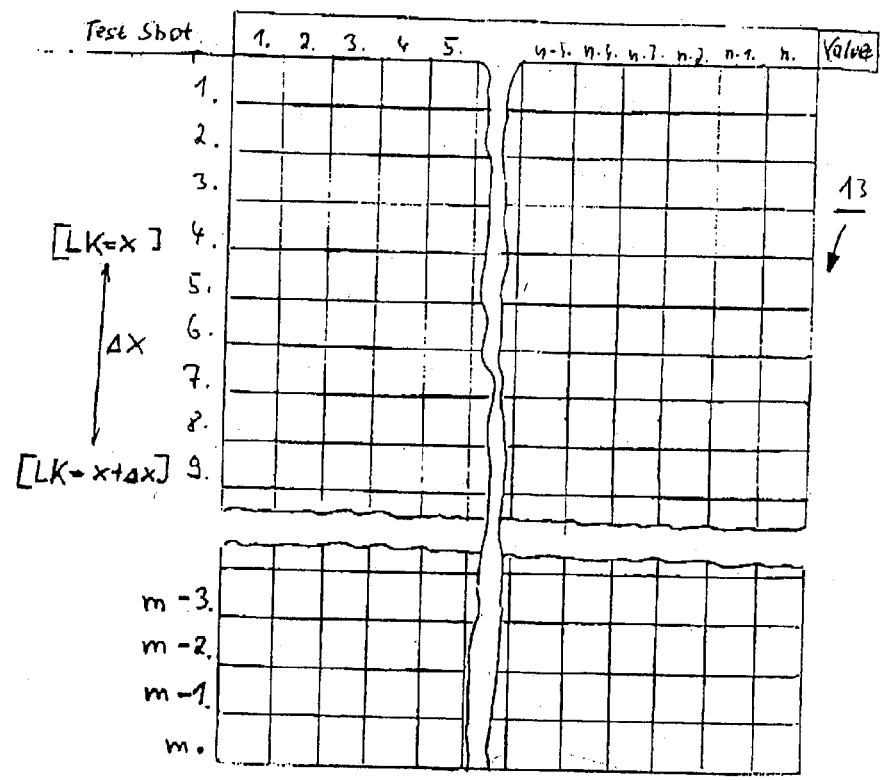
FIG. 5 is a schematic diagram of the evaluation process.

Referring now to FIG. 5, there is illustrated schematically the evaluation process according to the invention. The evaluation unit includes a data memory 13 arranged in the form of a matrix. The received signals digitized for each test shot are inputted in the data memory 13. For example, 50 values are inputted per test shot, so that n=50. In a same manner, in a next subjacent line, digitized received signals of the second test shot are inputted and so on.

According to the differential technique of the invention, the inputted values of the forth test shot are compared with the values of the ninth test shot and then evaluated, whereby this fourth test shot corresponds to a length coordinate LK=X. The ninth test shot corresponds to the length coordinate LK=X+$\Delta$X, reflecting the further advance of the test object by the amount $\Delta$X. The advantage of the method according to the present invention resides in the fact that $\Delta$X can be freely selected independent of particular sensor configurations and adapted to the specific defect characteristic of the test object.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A method of detecting discontinuities on elongated workpieces, in particular tubes and bars, using ultrasound, comprising the steps of:

positioning a test object in relationship to a test head, moving the test object and the test head relative to one another;

transmitting reception signals generated in the test head to an evaluation unit and digitizing the signals, comparing the digitized signals of a test shot at a length position X with digitized signals of a test shot at a length position X+$\Delta$X, wherein $\Delta$X is a multiple of a shot distance, by evaluating a difference between the test shots.

2. The method of claim 1, wherein $\Delta$X is freely selectable.

3. The method of claim 1, wherein a limited number of signals is evaluated in the evaluation unit.

4. The method of claim 3, wherein the number of evaluated signals is in the range between 20 and 100.

5. The method of claim 1, wherein the test head is configured as an electrodynamic transducer, with the test object moving past the transducer in an axial direction without rotation, wherein the transmitting step includes providing per test cycle wave pulses, which are guided in the test object circumferentially in two directions and are received at a reception site which is offset relative to a transmission site by one quarter of the wavelength of the guide waves, wherein the site of reception and excitation of the wave pulses, which propagate simultaneously in both circumferential directions of the test object, is selected such that both uninterfered circulating waves destructively interfere at the site of the receiver, wherein for each clock cycle the reception signal and a burst signal having an identical frequency, a suitable time period and a suitable start delay are transmitted to a peak detector, and the amplitudes are digitized and evaluated in the evaluation unit.

6. The method of claim 1, wherein the transmitting step includes generating in alternating fashion in the test cycle wave pulses at two locations which are separated in circumferential direction, with the wave pulses circulating in both circumferential directions, wherein a site of reception for reflected pulses is different from a site for attenuated pulses, and wherein the respective sequence of received signals is evaluated separately.

* * * * *

UNITED STATES PATENT AND TRADEMARK OFFICE
CERTIFICATE OF CORRECTION

PATENT NO. : 6,843,131 B2
DATED : January 18, 2005
INVENTOR(S) : Graff et al.

It is certified that error appears in the above-identified patent and that said Letters Patent is hereby corrected as shown below:

<u>Title page,</u>
Item [73], should read as follows:
-- Assignee: Mannesmannröhren-Werke AG, Mülheim, Germany --

Signed and Sealed this

Tenth Day of May, 2005

JON W. DUDAS
*Director of the United States Patent and Trademark Office*